United States Patent
Balasubramanium et al.

(10) Patent No.: US 6,737,408 B1
(45) Date of Patent: May 18, 2004

(54) COMPOUNDS FOR CONTROL OF APPETITE, BLOOD PRESSURE, CARDIOVASCULAR RESPONSE, LIBIDO, AND CIRCADIAN RHYTHM

(75) Inventors: Ambikaipakan Balasubramanium, Cincinnati, OH (US); William T. Chance, Withamsville, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/618,361

(22) Filed: Jul. 18, 2000

Related U.S. Application Data

(60) Continuation-in-part of application No. 09/449,914, filed on Dec. 2, 1999, now Pat. No. 6,235,718, which is a division of application No. 08/907,403, filed on Aug. 7, 1997, now Pat. No. 6,013,633.

(51) Int. Cl.[7] .......................... A61K 38/05; A61K 38/06
(52) U.S. Cl. .......................... 514/18; 530/300; 530/331; 530/335; 530/344; 530/345; 514/19; 435/7.1
(58) Field of Search .............................. 530/331, 330, 530/334, 335, 344, 345; 514/18, 19; 435/7.1

(56) References Cited

U.S. PATENT DOCUMENTS

| | | |
|---|---|---|
| 3,842,067 A | 10/1974 | Dimitrios Sarantakis |
| 3,862,925 A | 1/1975 | Sarantakis et al. |
| 3,972,859 A | 8/1976 | Fujino et al. |
| 4,105,603 A | 8/1978 | Vale, Jr. et al. |
| 4,244,946 A | 1/1981 | Rivier et al. |
| 4,297,346 A | 10/1981 | Rips et al. |
| 4,415,558 A | 11/1983 | Vale, Jr. et al. |
| 4,490,364 A | 12/1984 | Rivier et al. |
| 4,839,343 A | 6/1989 | Waeber et al. |
| 4,870,009 A | 9/1989 | Evans et al. |
| 5,270,302 A | 12/1993 | Shiosaki et al. |
| 5,328,899 A | 7/1994 | Boublik et al. |
| 5,410,018 A * | 4/1995 | Spindel et al. ............... 530/300 |
| 5,993,843 A * | 11/1999 | Sakurada et al. ............ 424/409 |
| 6,235,718 B1 * | 5/2001 | Balasubramanium et al. . 514/18 |

FOREIGN PATENT DOCUMENTS

| | | | | |
|---|---|---|---|---|
| EP | 288965 | * | 4/1988 | ............ C07K/5/00 |
| EP | 0268297 A2 | | 5/1988 | |
| EP | 0381340 A2 | | 8/1990 | |
| WO | WO 9103494 | * | 3/1991 | ............ C07K/17/00 |

OTHER PUBLICATIONS

*IUPAC–IUB Commission on Biochemical Nomenclature A One–Letter Notation for Amino Acid Sequences Tentative Rules*, The Journal of Biological Chemistry, vol. 243, No. 13, Jul. 10, 1968, 3557–3359.

D. De Wied (Ed.), *Neuropeptides, Basics and Perspectives*, Elsevier Science Publishers, The Netherlands, 1990, 175–351.

A.R. Gennaro et al. (Eds.), *Remington's Pharmaceutical Sciences*, Mack Publishing Company, Easton, PA, 1990, 931, 1012, 1021, 1120, 1164, 1286, 1298, 1305–1308, 1310–1311, 1313–1314, 1316–1317, 1320, 1324, 1329.

(List continued on next page.)

*Primary Examiner*—Christopher S. F. Low
*Assistant Examiner*—Chih-Min Kam
(74) *Attorney, Agent, or Firm*—Wood, Herron & Evans, L.L.P.

(57) ABSTRACT

This invention relates generally to dipeptides and tripeptides and to methods for pharmaceutical treatment of mammals using analogs of such dipeptides and tripeptides. More specifically, the invention relates to tripeptides and their analogs, to pharmaceutical compositions containing such dipeptides and tripeptides and to methods of treatment of mammals using such dipeptides and tripeptides. In addition, the invention relates to methods of treatment of mammals using such dipeptides and tripeptides for control of appetite, blood pressure, cardiovascular response, libido, and circadian rhythm.

12 Claims, 2 Drawing Sheets

OTHER PUBLICATIONS

E. Gross et al. (Eds.), *The Peptides, vol. 1, Major Methods of Peptide Bond Formation*, Academic Press, Inc., New York, San Francisco, London, 1979, 26–52, 125–126, 156–174, 242–260, 293–304, 336–362.

E. Gross et al. (Eds.), *The Peptides, vol. 3, Protection of Functional Groups in Peptide Synthesis*, Academic Press, Inc., New York, London, Toronto, Sydney, San Francisco, 1981, 1–99, 101–136, 203–252.

M. Heilig et al., *Neuropeptide Y: an overview of central distribution, functional aspects, and possible involvement in neuropsychiatric illnesses*, Acta Psychiatr. Scand., vol. 82, 1990, 95–114.

G. Poste et al., *Lipid Vesicles as Carriers for Introducing Biologically Active Materials into Cells*, Methods in Cell Biology, vol. XIV, Academic Press, New York, N.Y., 1976, 33–71.

J.M. Stewart et al., *Solid Phase Peptide Synthesis*, W.H. Freeman and Company, San Francisco, 1969.

J.D. Wilson, M.D. et al., *Harrison's Principles of Internal Medicine, 12th Ed.*, McGraw–Hill, Inc., 1991, Chaps. 15, 65–67, 69, 75–76, 84–86, 151, 182, 185, 190, 196, 301, 316–317, 319, 321–322, 369, 371–372.

A. Balasubramaniam et al., *Characterization of Neuropeptide Y Binding Sites in Rat Cardiac Ventricular Membranes*, Peptides, vol. 11, 1990, pp. 545–550.

A. Balasubramanium et al., *Synthesis and biological properties of 4–norleucine–neuropeptide Y; secondary structure of neuropeptide Y*, Biochimica et Biophysica Acta, vol. 997, 1989, pp. 176–181.

Elizabeth N. Barnes et al., *The Fine Structure of Continuous Human Neuroblastoma Lines SK–N–SH, SK–N–BE(2), and SK–N–MC.*, In Vitro, vol. 17, No. 7, Jul. 1981, pp. 619–631.

Ulrich Bickel et al., *Synthesis and Bioactivity of Monobiotinylated DALDA: A Mu–Specific Opioid Peptide Designed for Targeted Brain Delivery*, Journal of Pharmacology and Experimental Therapeutics, vol. 268, No. 2, 1994, pp. 791–796.

D. Bleakman et al., *Neuropeptide Y inhibits $Ca^2$ + influx into cultured dorsal root ganglion neurones of the rat via a $Y_2$ receptor*, Dept. of Pharmacological and Physiological Sciences, University of Chicago, Mar. 11, 1991, pp. 1781–1789.

W.T. Chance et al., *Pertussis Toxin Inhibits Neuropeptide Y–Induced Feeding in Rats*, Peptides, vol. 10, 1989, pp. 1283–1286.

S.T. Cheung et al., *N–Methylamino acids in peptide synthesis, V. The synthesis of N–tert–butyloxycarbonyl, N–methylamino acids by N–methylation*, Can. J. Chem., vol. 55, 1997, pp. 906–910.

Lars Grundemar et al., *Characterization of Receptor Types for Neuropeptide Y and Related Peptides*, in William F. Colmers et al. (ed.), *The Biology of Neuropeptide Y and Related Peptides*, Humana Press Inc., 1993, pp. 197–239.

David H. Coy et al., *Solid Phase Reductive Alkylation Techniques in Analogue Peptide Bond and Side–Chain Modification*, Tetrahedron, vol. 44, No. 3, 1988, pp. 835–841.

Yvan Dumont et al., *Neuropeptide Y and Neuropeptide Y Receptor Subtypes in Brain and Peripheral Tissues*, Progress in Neurobiology, vol. 38, 1992, pp. 125–167.

Jean–Alain Fehrentz et al., *An Efficient Synthesis of Optically Active α–(t–Butoxycarbonylamino)–aldehydes from α–Amino Acids*, Communications, Aug., 1983, pp. 676–678.

James F. Flood et al., *Dissociation of the Effects of Neuropeptide Y on Feeding and Memory: Evidence for Pre–and Postsynaptic Mediation*, Peptides, vol. 10, 1989, pp. 963–966.

Roger M. Freidinger et al., *Synthesis of 9–Fluorenylmethyloxycarbonyl–Protected N–Alkyl Amino Acids by Reduction of Oxazolidinones*, J. Org. Chem., vol. 48, 1983, pp. 77–81.

Jannie Fuhlendorff et al., *[$Leu^{31}$, $Pro^{34}$] Neuropeptide Y: A specific $Y_1$ receptor agonist*, Proc. Natl. Acad. Sci., vol. 87, Jan. 1990, pp. 182–186.

Glover et al., *Conformational studies on the pancreatic polypeptide hormone family*, Eur. J. Biochem. vol. 142, 1985, pp. 379–385.

Eric A. Gordon et al., *Characterization of Functional Neuropeptide Y Receptors in a Human Neuroblastoma Cell Line*, Journal of Neurochemistry, International Society for Neurochemistry, 1990, pp. 506–513.

M. Heilig et al., *Neuropeptide Y: an overview of central distribution, functional aspects, and possible involvement in neuropsychiatric illnesses*, Dept. of Psychiatry and Neurochemistry, University of Lund, Lund, Sweden, Mar. 17, 1990, pp. 95–114.

Joseph Hinson et al., *Neuropeptide Y stimulates inositol phospholipid hydrolysis in rat brain miniprisms*, Brain Research, vol. 446, 1988, pp. 379–382.

Jan M. Lundberg et al., *Neuropeptide Y receptor in pig spleen: binding characteristics reduction of cyclic AMP formation and calcium antagonist inhibition of vasoconstriction*, European Journal of Pharmacology, vol. 145, 1988, pp. 21–29.

R.B. Merrifield, *Solid Phase Peptide Synthesis. I. The Synthesis of a Tetrapeptide*, J. Amer. Chem. Soc., vol. 85, Jul. 20, 1963, pp. 2149–2154.

Martin C. Michel, *Receptors for neuropeptide Y: multiple subtypes and multiple second messengers*, TiPS, vol. 12, Oct. 1991, pp. 389–394.

Shin–ichi Mihara et al., *Neuropeptide Y.induced intracellular $Ca^{2+}$ increases in vascular smooth muscle cells*, FEBS Letters, vol. 259, No. 1, Dec. 1989, pp. 79–82.

Harvey J. Motulsky et al., *Neuropeptide Y Mobilizes $Ca^{2+}$ and inhibits adenylate cyclase in human erythroleukemia cells*, Amer. J. of Physiol., 1988, pp. E880–E885.

William M. Pardridge et al., *Endorphin Chimeric Peptides: Transport through the Blood–Brain Barrier in Vivo and Cleavage of Disulfide Linkage by Brain*, Endocrinology, vol. 126, 1990, pp. 977–984.

B. Penke et al., *New Synthetic Approach to Peptide Sulfate Esters. Synthesis and Biological Activities of CCK Analogs*, Synthesis of Peptides: Methods, Proceedings of the 8th American Peptide Symposium, Rockford, IL, 1983, pp. 119–122.

Marc Rodriguez et al., *Synthesis and Biological Activities of Pseudopeptide Analogues of the C–Terminal Heptapeptide of Cholecystokinin. On the Importance of the Peptide Bonds*, J. Med. Chem., vol. 30, 1987, pp. 1366–1373.

Y. Sasaki et al., *Solid Phase Synthesis of Peptides Containing the $CH_2NH$ Peptide Bond Isostere*, Peptides, vol. 8, 1987, pp. 119–121.

Eberhard Schroder et al., *The Peptides, Vol, 1, Methods of Peptide Synthesis*, Academic Press, 1965, pp. 72–75.

Thue W. Schwartz et al., *Signal Epitopes in the Three-Dimensional Structure of Neuropeptide Y: Interaction with $Y_{12}$ $Y_{22}$ and Pancreatic Polypeptide Receptors*, in Central and Peripheral Significance of Neuropeptide Y and its Related Peptides, (Janet M. Allen et al., eds.), Annuals of New York Academy of Sciences, vol. 611, 1990, pp. 35–47.

Soren P. Sheikh et al., *Localization of $Y_1$ receptors for NPY and PYY on vascular smooth muscle cells in rat pancreas*, Am. J. Physiol., vol. 260, 1991, pp. G250–G257.

Soren P. Sheikh et al., *$Y_2$–type receptors for peptide YY on renal proximal tubular cells in the rabbit*, Am. J. Physiol., vol. 26, 1989, pp. F978–F984.

Soren P. Sheikh et al., *Structural Characterization of $Y_1$ and $Y_2$ Receptors for Neuropeptide Y and Peptide YY by Affinity Cross–linking*, J. Biol. Chem, vol. 265, No. 14, May 15, 1990, pp. 8304–8310.

R.T. Shuman et al., *Structure–Activity Studies of Enkephalin Tetrapeptides*, in Peptides: Proceedings of the $7^{th}$ American Peptide Symposium, Rockford, IL, 1981, pp. 617–621.

Anders Unden et al., *Neuropeptide Y receptor in the rat brain*, Eur. J. Biochem., vol. 145, 1984, pp. 525–530.

Claes Wahlestedt et al., *Evidence for different pre– and post–junctional receptors for neuropeptide Y and related peptides*, Regulatory Peptides, vol. 13, 1986, pp. 307–318.

Mary W. Walker et al., *$^{125}I$–Neuropeptide Y and $^{125}I$–Peptide YY Bind to Multiple Receptor Sites in Rat Brain*, Molecular Pharmacology, vol. 34, Sep. 8, 1988, pp. 779–792.

Anita Westlind–Danielson et al., *Neuropeptide Y receptors and the inhibition of adenylate cyclase in the human frontal and temporal cortex*, Neuroscience Letters, vol. 74, 1987, pp. 237–242.

\* cited by examiner

SEQUENCE LISTING

```
<160> NUMBER OF SEQ ID NOS: 7

<210> SEQ ID NO 1
<211> LENGTH: 36
<212> TYPE: PRT
<213> ORGANISM: Homo sapiens

<400> SEQUENCE: 1

Tyr Pro Ser Lys Pro Asp Asn Pro Gly Glu Asp Ala Pro Ala Glu
                 5                  10                  15
Asp Met Ala Arg Tyr Tyr Ser Ala Leu Arg His Tyr Ile Asn Leu
                20                  25                  30
Ile Thr Arg Gln Arg Tyr
                35

<210> SEQ ID NO 2
<211> LENGTH: 4
<212> TYPE: PRT
<213> ORGANISM: Artificial Sequence
<220> FEATURE:
<221> NAME/KEY: MOD RES
<222> LOCATION: (1)...(4)
<223> OTHER INFORMATION: The compound is a dimer of the sequence listing
      and the dimer is formed by a disulfide bond. Artificial
      sequence is completely synthesized.
```

```
<400> SEQUENCE: 2

Cys Trp Arg Tyr
  1

<210> SEQ ID NO 3
<211> LENGTH: 7
<212> TYPE: PRT
<213> ORGANISM: Artificial Sequence
<220> FEATURE:
<221> NAME/KEY: MOD RES
<222> LOCATION: (1)...(7)
<223> OTHER INFORMATION: Xaa at location 1 represents Dap.  Artificial
      sequence is completely synthesized.

<400> SEQUENCE: 3

Xaa Ile Trp Arg Glu Arg Tyr
  1               5

<210> SEQ ID NO 4
<211> LENGTH: 7
<212> TYPE: PRT
<213> ORGANISM: Homo sapiens

<400> SEQUENCE: 4

Leu Ile Trp Arg Glu Arg Tyr
  1               5

<210> SEQ ID NO 5
<211> LENGTH: 5
<212> TYPE: PRT
<213> ORGANISM: Artificial Sequence
<220> FEATURE:
<221> NAME/KEY: MOD RES
<222> LOCATION: (1)...(5)
<223> OTHER INFORMATION: Xaa at location 3 represents Nva.  Artificial
      sequence is completely synthesized.

<400> SEQUENCE: 5

Trp Arg Xaa Arg Tyr
  1               5

<210> SEQ ID NO 6
<211> LENGTH: 6
<212> TYPE: PRT
<213> ORGANISM: Homo sapiens

<400> SEQUENCE: 6

Trp Arg Tyr Trp Arg Tyr
  1               5

<210> SEQ ID NO 7
<211> LENGTH: 6
<212> TYPE: PRT
<213> ORGANISM: Homo sapiens

<400> SEQUENCE: 7

Trp Arg Tyr Trp Arg Tyr
  1               5
```

COMPOUNDS FOR CONTROL OF APPETITE, BLOOD PRESSURE, CARDIOVASCULAR RESPONSE, LIBIDO, AND CIRCADIAN RHYTHM

This application is a continuation-in-part of U.S. application Ser. No. 09/449,914, filed on Dec. 2, 1999, now U.S. Pat. No. 6,235,718, issued May 22, 2001, which is a divisional of U.S. application Ser. No.08/907,403, filed on Aug. 7, 1997, now U.S. Pat. No. 6,013,633, issued Jan. 11, 2000.

The U.S. Government has a paid-up license in this invention and the right in limited circumstances to require the patent owner to license others on reasonable terms as provided for by the terms of Grant/Contract No. GM47122 awarded by the National Institutes of Health.

BACKGROUND OF THE INVENTION

This invention relates generally to dipeptides and tripeptides and to methods for pharmaceutical treatment of mammals using analogs of such dipeptides and tripeptides. More specifically, the invention relates to tripeptides and their analogs, to pharmaceutical compositions containing such dipeptides and tripeptides and to methods of treatment of mammals using such dipeptides and tripeptides. In addition, the invention relates to methods of treatment of mammals using such dipeptides and tripeptides for control of appetite, blood pressure, cardiovascular response, libido, and circadian rhythm.

1. Appetite and Obesity

Obesity is a major disorder affecting as much as one third of the North American population. Several studies have shown that such individuals are at increased risk in developing cardiovascular disease (hypertension and hypercholesterolemia), diabetes and several types of cancer. The effective treatment of obesity, however, remains a largely unachieved goal. Existing pharmacotherapeutic approaches to weight loss involve the use of amphetamine-based agents such as amphetamine, diethylpropion, mazindol and fenfluramine which act directly on the CNS to lower food intake by modulating dope minergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions other drugs such as MAO inhibitors and antihypertensivcs. There is also a subpopulation of obese patients that is refractory to present anorectic drug treatments. The medical need is high for an effective anorectic agent which overcomes the above disadvantages of existing therapies. Of particular need are agents which act by alternative mechanisms to modulate food intake and/or metabolism.

2. Neuropeptide Y ("NPY")

Throughout this application, various publications are referenced. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (De Wied, D. In: Neuropeptides: Basics and Perspectives (Elsevier, Amsterda in-New York-Oxford), 1990.). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. NPY is an important regulator in both the central and peripheral nervous systems (Heilig, M. and E. Widerlov. Neuropeptide Y: an overview of central distribution, functional aspects, and possible involvement of neuropsychiatric illnesses. Acta Psychiatr. Scand. 82:95–114 (1990).) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and has contributed to vasoconstriction. NPY binding sites have been identified in a variety of tissues, including spleen (Lundberg, J. M., A. Hemsen, 0. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol. 145:21–29 (1988)), intestinal membranes, brain (Hinson, J., C. Rauh, and J. Coupet. Neuropeptide Y stimulates inositol phospholipid hydrolysis in rat brain microprisms. Brain RESPONSE. 446:379–382 (1988)), aortic smooth muscle (Mihara, S., Y. Shigeri, and M. Fujimoto. Neuropeptide Y-induced intracellular Ca2+ increase in vascular smooth muscle cells. FEBS Lett. 259: 79–82 (1989)), kidney, testis, and placenta (Dumont, Y. , J. C. Martel, A. Foumier, S. St.-Pierre, and R. Quiron. Neuropeptide Y and neuropeptide Y receptor subtypes in brain and peripheral tissues. Prog. Neurobiol. 38:125–167 (1 992)). In addition, binding sites have been reported in a number of rat and human cell lines (e.g. Y1 in SK-N-MC, MC-IXC, CHP-212, and PC12 cells; Y2 in SK-N-Be(2), CHP-234, and SMS-MSN)(Grundemar, L., S. P. Sheikh, and C. Wahlestedt, In: The Biology of Neuropeptide Y and Related Peptides. (Humana Press, Inc , Totawa, N.J.), (1992)).

NPY forms a family (called the pancreatic polypeptide family) together with pancreatic polypeptide (PP) and peptide YOSHIOKA (PYY) which all consist of 36 amino acids and have a common tertiary structure, the so-called PP-fold (Glover, I. D., D. J. Barlow, J. E. Pitts, S. P. Wood, I. J. Tickle, T. L. Blundell, K. Tatemoto, J. R. Kimmel, A. Wollmer, W. Strassburger, and Y. -S. Zhang. Conformational studies of the pancreatic polypeptide hormone family. Eur. J. Biochem. 142:379–385 (1985)). Specific features of this family include a polyproline helix in residues 1 through 8, beta-turn in residues 9 through 14, an alpha-helix in residues 15 through 30, an outward-projecting C-terminus in residues 30 through 36, and a carboxy terminal amide which appears to be critical for biological activity (Schwartz, T. W., J. Fuhlendorff, L. L. Kjems, M. S. Kristensen, M. Vervelde, M. O'Hare, J. L. Krstenansky, and B. Bjornholm. Signal epitopes in the three-dimensional structure of neuropeptide Y. Ann. N.Y. Acad. Sci. 611:35–47 (1990)). The C-terminal amidated residue of these peptides is essential for biological activity (Wahlestedt et at., 1986). Studies with peptide fragments of NPY have indicated that multiple NPY receptor subtypes exist (Wahlestedt, C., N. Yanaihara, and R. Hakanson. Evidence for different pre- and postjunctional receptors for neuropeptide Y and related peptides. Regul. Pept. 13:307–318 (1986)). Three major NPY receptor subtypes (Y1, Y2 and Y3) have been defined by pharmacological criteria, with a fourth "atypical" Y1 receptor that has been proposed to regulate feeding behavior. One of the key pharmacological features which distinguish Y1 and Y2 is the fact that the Y1 receptor (and not the Y2 receptor) responds to an analog of NPY modified at residues 31 and 34 ([Leu31,Pro34]NPY), whereas the Y2 receptor (and not the Y1 receptor) has high affinity for the NPY peptide carboxyl-terminal fragment NPY-(13–36)(Fuhlendorff, J., U. Gether, L. Aakerlund, N. Langeland-Johansen, H .. Thogersen, S. G. Melberg, U. B. Olsen, O. Thastrup, and T. W. Schwartz. [Leu31,Pro34]Neuropeptide Y: A specific Y1 receptor agonist. Proc. Natl. Acad. Sci. USA 87:182–186 (1990)).

Experimental and clinical observations have supported the concept that neuropeptides play central roles in neurotransmission as well as the regulation of secretory functions of adenohypophysial, pancreatic, adrenalcortical and gut cells. Among the thirty or so neuropeptides that have been implicated in neuronal function in the mammalian central nervous system, several have also been suggested to function as neurotransmitters or neuromodulators primarily in afferent neurons.

An additional action of NPY is to decrease cardiac contractility (inotropy). This is an extremely important action of NPY, because it is known that, under many circumstances in which inotropy is decreased, diseases of life-threatening importance, e.g. congestive heart failure and cardiogenic shock, are associated with probable increased release of NPY into the blood. Prevention of NPY release, using a presynaptic NPY agonist, or NPY's action, using a postsynaptic NPY antagonist, may be beneficial in these disease states.

NPY has also been reported to produce coronary artery vasoconstriction and thereby may decrease myocardial blood flow resulting in myocardial ischemia. Such a circumstance can result in angina pectoris or, under more severe circumstances, may result in myocardial infarction and death. In recent years, several classes of drugs have proven effective in dilating coronary arteries to prevent such events. The use of analogs of NPY are expected to prove useful in treatment of such problems.

U.S. Pat. No. 4,297,346, Rips, discloses therapeutic agents referred to as 'pseudopeptides' being formed from at least one peptide radical connected by a peptide bond to a therapeutically active molecule or derivative of a therapeutically active molecule. The therapeutic agents of the invention may be in the form of derivatives such as salts, esters and amides. The basis of action of the agents of the invention is the ability of the agents of the invention to cross bodily biological barriers because of the basically peptide structure of the agents. The invention also includes the preparation of the agents of the invention.

U.S. Pat. No. 5,328,899, Boublik et al., issued Jul. 12, 1994, discloses NPY peptide analogs. Human Neuropeptide Y (NPY) has the formula: H-Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg-Tyr-NH2 (SEQ ID NO:1). Porcine and rat NPY have the same sequence except for Leu instead of Met in the 17-position. Porcine PYY is homologous having 11 different residues. NPY analogs and N-terminally-shortened fragments, e.g. NPY(18–36), which contain one or more specific D-isomer substitutions for the naturally occurring residues (as well as pharmaceutically acceptable salts thereof), dispersed in a pharmaceutically acceptable liquid or solid carrier, can be administered to mammals, including humans, to substantially lower blood pressure over an extended period of time or to counteract hypertension.

U.S. Pat. No. 4,839,343, Waeber et al., issued Jun. 13, 1989, discloses a preparation containing hexatriacontapeptides suitable for intravenous administration to human or other animal subjects which are effective in treating life-threatening hypotension as encountered in bacteremic, anaphylactic or cardiogenic shock.

Several references have disclosed CCK agonists or analogs of CCK-8. For example, U.S. Pat. No. 4,490,364, issued Dec. 25, 1984 to Rivier, discloses heptapeptide, octapeptide and nonapeptide analogs of CCK-8 as CCK agonists for stimulating gallbladder contractions, arresting the secretion of gastric acid and treating convulsions. J. D. Rosarnond in European Patent Application EP381,340, published Aug. 8, 1990, and in European Patent Application EP268,297, published May 25, 1988, discloses hepta- and octapeptides with sulfate ester groups which are useful for treating obesity.

U.S. Pat. No. 5,270,302, Shiosaki et al., issued Dec. 14, 1993, discloses derivatives of tetrapeptides as CCK agonists which are selective and potent Type-A CCK receptor agonists useful in the treatment of gastrointestinal disorders (including gallbladder disorders), central nervous system disorders, insulin-related disorders and pain, as well as in appetite regulation.

None of these references individually or collectively teach or suggest the present invention.

SUMMARY OF THE INVENTION

This invention relates generally to dipeptides and tripeptides and to methods for pharmaceutical treatment of mammals using analogs of such dipeptides and tripeptides. More specifically, the invention relates to tripeptides and their analogs, to pharmaceutical compositions containing such dipeptides and tripeptides and to methods of treatment of mammals using such dipeptides and tripeptides. In addition, the invention relates to methods of treatment of mammals using such dipeptides and tripeptides for control of appetite, blood pressure, cardiovascular response, libido, and circadian rhythm.

The present invention is directed to neuropeptide Y ("NPY") receptor antagonists and agonists. In one aspect, the present invention features compounds having the formula:

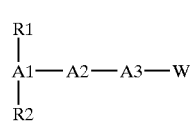

(I)

wherein:
each R1 and R2, independently, is H, C1–C12 alkyl (e.g., methyl), C6–C18 aryl (e.g., phenyl), C1–C18 acyl (e.g., formyl, acetyl, and myristoyl), C7–C18 aralkyl (e.g., benzyl), C7–C18 alkaryl (e.g., p-methylphenyl) or a dihydrotrigonellinate group;

A1 is a D or L-amino acid selected from the group consisting of Cys, Leu, Dap (1,2-Diaminopropionic acid), Trp, Gln, a tethered amino acid with an indole ring (e.g., N-Me-Trp), Phe, Hyp, any Trp derivative (e.g., 2 chlorotroptophan, or Tcc); CaMe-Trp, CaMe-Gln, Des-amino-Trp, Pyr (Pyroglutamic acid), Bth, Nal, Tcc, Asn, Nva, Abu, Tyr, Tic-OH, Phe, Tip (1,2, 3,4-tetrahydronorharman-3-carboxylic acid), and Dip;

A2 is a D or L-amino acid selected from the group consisting of Cys, Trp, Arg, N-Me-Arg, CαMe-Arg, Orn, Cit, hArg(R)2 [where R is selected from the group consisting of hydrogen, alkyl, aryl, aralkyl, or alkylaryl], Lys-ε-NH-R [where R is selected from the group consisting of hydrogen, alkyl, aryl, aralkyl, or alkylaryl];

A3 is a D or L-amino acid selected from the group consisting of Glu, N-Me-Tyr, CαMe-Tyr, Tic-OH, Tic, Dip, Trp, Phe, des -arboxylic-Tyr (tyramine), and Tyr-(R) [where R is hydrogen or a lipophilic group, e.g., myristoyl, cholesteryl, t.Bu, etc.];

W is —OH, —N—R3R4, or OR5 (where R3, R4, and R5, independently, is H, C1–C12 alkyl (e.g., methyl), C6–C18 aryl (e-g-, phenyl), C1–C12 acyl (e.g., formyl, acetyl, and myristoyl), C7–C18 aralkyl (e.g., benzyl), or C7–C18 alkaryl (e.g., p-methylphenyl); or a pharmaceutically acceptable salt thereof; and each bond between two amino acids or amino acid derivatives, represented by a dash ("–"), can be either a peptide bond or a pseudopeptide bond or a pharmaceutically acceptable salt thereof.

Preferred compounds of formula (I) include those in which A1 is Trp or a pharmaceutically acceptable salt thereof.

In another aspect, the invention features a compound having the formula:

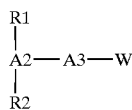

(II)

In another aspect, the invention features a compound having the formula:

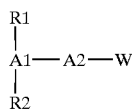

(III)

In another aspect, the invention features a compound having the formula:

Cyclo-[-A1-A2-A3-], (IV)

Cyclo-[-A1-A2-A3-A1-A2-A3-], or (V)

Cyclo-[-A1-A2-A3-A3-A2-A1-]. (VI)

In another aspect, the invention features a compound having the formula:

Ac-[A1-A2-A3]$_n$-NH$_2$ (VII)

(n=1, 2, 3) (A Tandem Peptide)

In another aspect, the invention features dimers of compounds having the formula (I–III). Dimers may be prepared by dimerizing compounds of formula (I–III) with dicarboxylic acids (e.g., succinic acid), cystine, or diaminodicarboxylic acid (e.g., 2,6-diaminopimelic acid).

In another aspect, the invention features a compound having the formula of (I–VII) conjugated to carriers.

In another aspect, the invention features a method of controlling the blood pressure of a subject experiencing hypertension.

In another aspect, the invention features a method of controlling a NPY physiological response in the cardiovascular system, including blood pressure, of a subject.

In other preferred embodiments, a compound of formula (selected from I thru VII) may have one or more pseudopeptide bonds. The abbreviation psi ("ψ") is the designation for a pseudopeptide bond (e.g., ("ψ")("CH$_2$NH") indicates that the amide ("—C(O)NH—") bond of a peptide has been replaced by the reduced form ("—CH$_2$NH—")).

In other preferred embodiments, a therapeutically effective amount of a compound of formula (selected from I thru VII) and a pharmaceutically acceptable carrier substance together form a therapeutic composition capable of suppressing an NPY mediated physiological response.

DETAILED DESCRIPTION OF THE INVENTION

Figure 1:
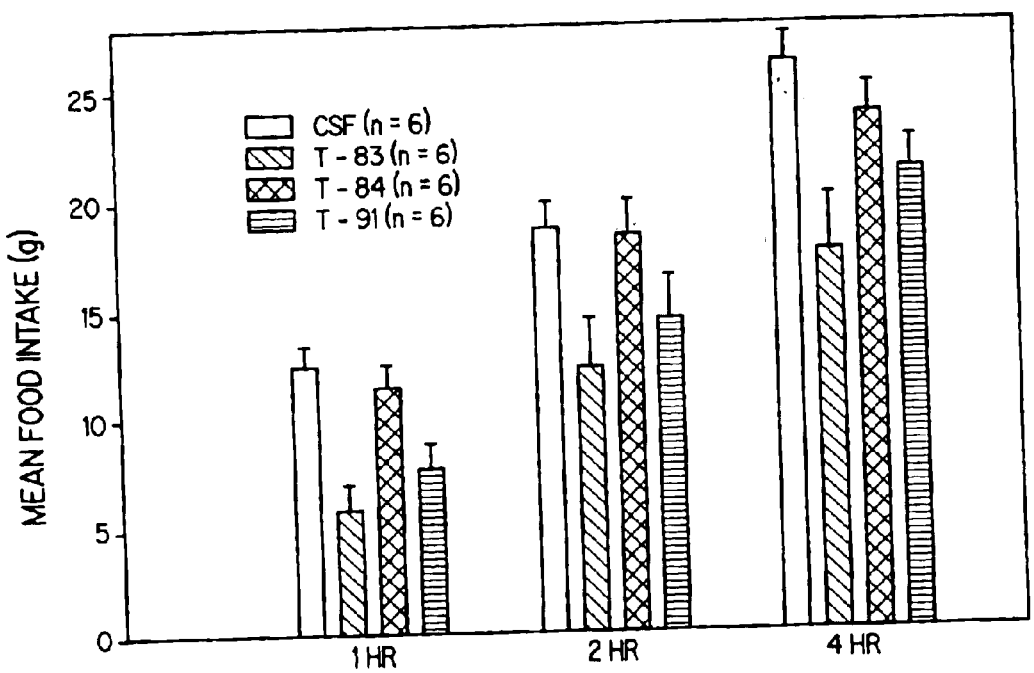
FIG. 1. A graph representing the feeding patterns of animals treated with the tripeptides by intrahypothalamic cannulae. The compounds tested include control (artificial cerebral spinal fluid, CSF), T-83 (Ac-Tcc-Arg-Tyr-NH$_2$), T-84 (N-a-indole-3-acetyl-Arg-Tyr-NH$_2$), and T-91 (Ac-Trp-Arg-Tic(OH)-NH$_2$).

The present invention is directed to neuropeptide Y ("NPY") receptor antagonists and agonists. In one aspect, the present invention features compounds having the formula:

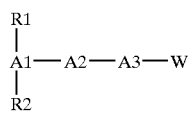

(I)

wherein:

each R1 and R2, independently, is H, C1–C12 alkyl (e.g., methyl), C6–C18 aryl (e.g., phenyl), C1–C18 acyl (e.g., formyl, acetyl, and myristoyl), C7–C18 aralkyl (e.g., benzyl), C7–C18 alkaryl (e.g., p-methylphenyl) or a dihydrotrigonellinate group;

A1 is a D or L-amino acid selected from the group consisting of Cys, Leu, Dap, Trp, Gln, a tethered amino acid with an indole ring (e.g., N-Me-Trp), Phe, Hyp, any Trp derivative (e.g., 2 chlorotroptophan, or Tcc); CαMe-Trp, CαMe-Gln, Des-amino-Trp, Pyr, Bth, Nal, Tcc, Asn, Nva, Abu, Tyr, Tic-OH, Phe, Tip, and Dip;

A2 is a D or L-amino acid selected from the group consisting of Cys, Trp, Arg, N-Me-Arg, CαMe-Arg, Orn, Cit, hArg(R)2 [where R is selected from the group consisting of hydrogen, alkyl, aryl, aralkyl, or alkylaryl], Lys-ε-NH-R [where R is selected from the group consisting of hydrogen, alkyl, aryl, aralkyl, or alkylaryl];

A3 is a D or L-amino acid selected from the group consisting of Glu, N-Me-Tyr, CαMe-Tyr, Tic-OH, Tic, Dip, Trp, Phe, des-carboxylic-Tyr (tyramine), and Tyr-(R) [where R is hydrogen or a lipophilic group, e.g., myristoyl, cholesteryl, t.Bu, etc.];

W is —OH, —N—R3R4, or OR5 (where R3, R4, and R5, independently, is H, C1–C12 alkyl (e.g., methyl), C6–C18 aryl (e-g-, phenyl), C1–C12 acyl (e.g., formyl, acetyl, and myristoyl), C7–C18 aralkyl (e.g., benzyl), or C7–C18 alkaryl (e.g., p-methylphenyl); or a pharmaceutically acceptable salt thereof; and each bond between two amino acids or amino acid derivatives, represented by a dash ("–"), can be either a peptide bond or a pseudopeptide bond or a pharmaceutically acceptable salt thereof.

Preferred compounds of formula (I) include those in which A1 is Try or a pharmaceutically acceptable salt thereof.

In another aspect, the invention features a compound having the formula:

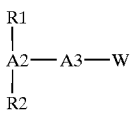
(II)

In another aspect, the invention features a compound having the formula:

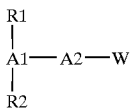
(III)

In another aspect, the invention features a compound having the formula:

Cyclo-[-A1-A2-A3-], (IV)

Cyclo-[-A1-A2-A3-A1-A2-A3-], or (V)

Cyclo-[-A1-A2-A3-A3-A2-A1-]. (VI)

In another aspect, the invention features a compound having the formula:

Ac-[A1-A2-A3]$_n$-NH$_2$ (VII)

(n=1, 2, 3) (A Tandem Peptide)

In another aspect, the invention features dimers of compounds having the formula I–III prepared by dimerizing the compound with dicarboxylic acids (e.g., succinic acid), cystine, or diaminodicarboxylic acid (e.g., 2,6-diaminopimelic acid).

In another aspect, the invention features a compound having the formula of (I) could be conjugated to carriers, e.g., cationized albumin (Endocrinology 126:977–984 (1990); J. Pharmacol Exp. Therao. 268:791–796 (1994), incorporated herein by reference in their entirety) or polylysine, e.g., MAP.

In another aspect, the invention features a method of controlling the blood pressure of a subject experiencing hypertension which comprises administering to said subject the compound of formula (I–VII).

In another aspect, the invention features a method of controlling a NPY physiological response in the cardiovascular system, including blood pressure, of a subject comprising administering to said subject the compound of formula (I–VII).

In other preferred embodiments, a compound of formula (selected from I thru VII) may have one or more pseudopeptide bonds. The abbreviation psi ("ψ") is the designation for a pseudopeptide bond (e.g., ("ψ")("CH$_2$NH") indicates that the amide ("—C(O)NH—") bond of a peptide has been replaced by the reduced form ("—CH$_2$NH—") or less preferably that of C(O)NH is replaced with any of CH$_2$—S, CH$_2$—O, CH$_2$—CH$_2$, CH$_2$—CO, or CH$_2$CH$_2$). For example, Trp—("ψ")(CH$_2$NH)Lys represents a tryptophan residue bonded to a lysine residue wherein the amide bond is reduced. A detailed discussion of the chemistry of pseudopeptide bonds is given in Coy et at. (1988) *Tetrahedron* 44: 835–841, incorporated herein in its entirety by reference.

In other preferred embodiments, a therapeutically effective amount of a compound of formula (selected from I thru VII) and a pharmaceutically acceptable carrier substance, e.g., magnesium carbonate or lactose, together form a therapeutic composition capable of suppressing an NPY mediated physiological response. This composition can be in the form a pill, tablet, capsule, liquid, or sustained released tablet for oral administration; or a liquid for nasal administration as drops or spray; or a liquid for intravenous, subcutaneous, parenteral, or intraperitoneal administration.

Another preferred form for administration biodegradable sustained-release composition for intramuscular administration to a subject in need of the composition. Preferably, the composition includes a lipophilic salt and is suitable for administration in the form of an oil emulsion or dispersion to a subject in need of the composition.

In yet another aspect, the invention features methods for controlling an NPY mediated physiological response in a subject; such methods involve administering one or more of the above mentioned compounds to a subject in a dosage effective to control blood pressure, the appetite, the libido, cardiovascular function, and circadian rhythm.

The symbol A1, A2, A3, and the like; and Tyr, Lys or the like, as found in a peptide sequence herein stands for an amino acid residue, e.g., =N—CH(R)—CO— when it is at the N-terminus, or —NH—CH(R)—CO— when it is at any other position, where R denotes the side chain (or identifying group) of an amino acid or its residue. For example, R is CH$_2$COOH for Asp, R is —H for Gly, R is —CH$_2$OH for Ser, R is —CH3 for Ala and R is —CH$_2$CH$_2$CH$_2$CH$_2$NH$_2$ for Lys.

As set forth above and for convenience in describing this invention, the conventional and nonconventional abbreviations for the various amino acids are used. They are familiar to those skilled in the art; but for clarity are listed below. All peptide sequences mentioned herein are written according to the usual convention whereby the N terminal amino acid is on the left and the C-terminal amino acid is on the right. A short line between two amino acid residues indicates a peptide bond.

Abbreviations (common):

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine Lys=K=Lysine
Met=M=Methionine
Phe=F=Phenytalanine
Pro=P=Proline
Ser=S=Serine
Thr=T=Threonine
Trp=W=Tryptophan
Tyr=Y=Tyrosine
Val=V=Valine Abbreviations (uncommon):

Aoc=(8-aminooctanoic acid:
Orn=Ornithine
Nal=2-napthylalanine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=alpha-aminonormalbutyric acid
Dip=2,2-diphenylalanine
Ac$_6$c=1-aminocyclohexanecarboxylic acid
D-Pal=beta-(3-pyridyl)alanine;
Tcc=tetrahydrocarbolenecarboxylic acid
Abu=α-aminonormalbutyric acid
hArg(Pr)$_2$=N,N'-guanidino-(dipropyl)-homoarginine
Tic-OH=1,2,3,4 tetrahydroisoquinoline-7-hydroxy-3-arboxylic acid
Dip=3,3-diphenylalanine
2-Nal=3(2-naphthylalanine)
Tfp=Paratrifluoromethyl phenylalanine
Fla=3-(9-Fluorenyl)alanine
Flg=9-Fluorenylglycine
Cit=Citrutine
Adp=2,5-diaminoadipic acid
Pim=2,6-diaminopimelicacid
Sub=2,7-diaminosuberic acid The compounds of the invention are useful in treating any number of illnesses that involve eating disorders, cardiovascular function, alterations in sexual function, as well as disorders of sleep and circadian rhythms (see, e.g., *Harrison's Principles of Internal Medicine*, McGraw-Hill Inc., New York, 12th ed.).

Other features and advantages of the invention will be apparent from the following description of the preferred embodiments thereof, and from the claims.

The present invention is also directed to pharmaceutical compositions comprising a therapeutically-effective amount of a compound of formula (I–VII) and a pharmaceutically-acceptable carrier or diluent, as well as to a method of treating gastrointestinal disorders (including gallbladder disorders), central nervous system disorders, insulin-related disorders and pain, or of regulating appetite in humans and lower mammals, by administration of a compound of formula (I–VII).

The terms "C2–C4-alkenyl" and "C2–C6-alkenyl" as used herein refer to a 2 to 4 or 6 straight- or branched-chain of carbon atoms which contains a carbon-carbon double bond, such as allyl, propenyl, butanol, isoprenyl and the like.

The terms "C1–C18-alkyl" as used herein refer to straight or branched chain alkyl radicals having from 1 to 18 carbon atoms including, but not limited to, methyl, ethyl, propyl, isopropyl, butyl, isobutyl, sec-butyl, pentyl, neopentyl hexyl, and the like.

The term "C6–C18-aryl" as used herein refers to phenyl or to a "bicyclic carbocyclic" group or "bicyclic carbocycle" having two fused carbocyclic rings, each ring having 5, 6 or 7 carbon atoms, and each ring being fully saturated, partially saturated or aromatic. Bicyclic carbocyclic groups include, but are not limited to, naphthyl, tetrahydronaphthyl, decalin, indanyl, indenyl and the like.

The term "C7–C18-arylalkyl" as used herein refers to an aryl group appended to a C1–C4alkyl radical including, but not limited to, benzyl, phenethyl, naphthylmethyl and the like.

The term "bicyclic heterocycle" as used herein refers to a group having two fused rings, one or both of which are heterocyclic rings as defined herein. When both rings are not heterocyclic, the other ring is carbocyclic and is saturated, partially saturated or aromatic, preferably a benzene ring. Bicyclic heterocyclic groups can be unsubstituted or mono-substituted or disubstituted with substituents independently selected from hydroxy, halo, oxo (=O), amino, C1–C4-alkylamino, di-(C1–C4)-alkylamino, C1–C4-alkoxy, thio-C1–C4-alkoxy, carboxy, C1–C4-alkoxycarbonyl, C1–C4-alkyl, C3–C8-cycloalkyl, —OSO3H and halo-C1–C4-alkyl. Examples of bicyclic heterocycles include indole, 5-hydroxyindole, quinoline, isoquinoline, tetrahydroisoquinoline, quinoxaline, benzimidazole, benzofuran, and the like.

The term "cyclo-C3–C10-alkyl" as used herein refers to an aliphatic monocyclic of 3 to 10 or bicyclic group having 6 to 10 carbon atoms including, but not limited to, cyclopropyl, cyclobutyl, cyclopentyl, cyclohexyl, cyclooctyl, adamantyl, and the like.

The term "halo" or "halogen" as used herein refers to chloro, bromo, iodo or fluoro.

The term "halo-C1–C4-alkyl" as used herein refers to a lower alkyl radical in which one to three hydrogen atoms have been replaced by a halogen including, but not limited to, chloromethyl, 2-fluoroethyl, trifluoromethyl and the like.

The term "monocyclic heterocyclic group" or "monocyclic heterocycle" as used herein refers to any 3- or 4-membered ring containing a heteroatom selected from oxygen, nitrogen and sulfur, or a 5- or 6-membered ring containing carbon atoms and one, two or three nitrogen atoms; one nitrogen and one sulfur atom; or one nitrogen and one oxygen atom; wherein the 5-membered ring has 0–2 double bonds and the 6-membered ring has 0–3 double bonds; wherein the nitrogen and sulfur heteroatoms may optionally be oxidized; and wherein the nitrogen heteroatom may optionally be quaternized. Heterocycles include, but are not limited to, pyridyl, imidazolyl, furyl, thienyl, pyrazinyl, pyrrolyl, pyrimidyl and the like. Heterocyclics may be unsubstituted or mono- or disubstituted with substituents independently selected from hydroxy, halo, oxo (=O), amino, C1-C4-alkylamino, (C1–C4)2-alkylamino, C1–C4-alkoxy, thio-C1–C4-alkoxy, carboxy, C1–C4-alkoxycarbonyl, C1–C4-alkyl, C3–C8-cycloalkyl, —OSO$_3$H and halo-C1–C4-alkyl.

The compounds of formula (I) contain two or more asymmetric carbon atoms and thus can exist as pure diastereomers, mixtures of diastereomers, diastereomeric racemates or mixtures of diastereomeric racemates. The present invention includes within its scope all of the isomeric forms. In keeping with standard peptide nomenclature, J. Biol. Chem., 1969, 243:3557–59, abbreviations for amino acid residues are used herein.

It is noted that all amino acid residue sequences are represented herein by formulae whose left to right orientation is in the conventional direction of amino-terminus to carboxy-terminus.

Administration

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of excretion, drug combination, and the severity of the particular disease undergoing therapy.

However, generally speaking the following guidelines will suffice. When a compound of formula (I) is used as an agonist of NPY in a human subject, the total daily dose administered in single or divided doses may be in amounts, for example, from 0.001 to 1000 mg a day and more usually 1 to 1000 mg. Dosage unit compositions may contain such amounts of submultiples thereof to make up the daily dose.

The compounds useful in the present inventive method may be administered by any suitable means. One skilled in the art will appreciate that many suitable methods of administering the compounds to an animal in the context of the present invention, in particular a human, are available, and, although more than one route may be used to administer.a particular compounds, a particular route of administration may provide a more immediate and more effective reaction than another route.

The composition according to the present invention may be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for ex ample, potato starch or alginic acid; binding agents, for example, starch, gelatin or acacia; and lubricating agents, for example, magnesium stearate, stearic acid or talc. Other pharmaceutically acceptable excipients can be colorants, flavoring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed.

Formulations for oral use may also be presented as chewing tablets , or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the tetrapeptide of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation.

For parenteral use, the pharmaceutical compositions according to the invention may comprise the thermogenic compounds in the form of a sterile injection. To prepare such a composition, the compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For the rectal application, suitable dosage forms for a composition according to the present invention include suppositories (emulsion or suspension type), and rectal gelatin capsules (solutions or suspensions). In a typical suppository formulation, the compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For the nasal application typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavoring agents, preservatives, etc., are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

Examples of emulsifying agents are naturally occurring gums, e.g., gum acacia or gum tragacanth, naturally occurring phosphatides, e.g., soybean lecithin and sorbitan monooleate derivatives.

Examples of antioxidants are butylated hydroxy anisole (BHA), ascorbic acid and derivatives thereof, tocopherol and derivatives thereof and cysteine.

Examples of preservatives are parabens and benzalkonium chloride.

Examples of humectants are glycerin, propylene glycol, sorbitol and urea.

Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and AZONE®.

Examples of chelating agents are sodium EDTA, citric acid and phosporic acid.

Examples of gel forming agents are Carbopol, cellulose derivatives, bentonit, alginates, gelatin and PVP.

Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g., polyoxyethylene sorbitan monooleate (Tween).

The formulation and preparation of the above-mentioned compositions is well-known to those skilled in the art of pharmaceutical formulation. Specific formulation can be found in "Remington's Pharmaceutical Sciences" incorporated herein by reference.

In one aspect the present invention relates to a method for treatment of overweight or obesity in individuals, in particular in humans or for reducing the adipose tissue mass/lean mass body mass ratio of an individual, in particular a human or a domestic animal.

In the present context the term "overweight" is used as an indication of a body with a weight exceeding the "desirable weight", whereas the term "obesity" is used when the body weight is 20% or more above the "desirable weight". Desirable weights for humans are given by the Council on Scientific Affairs (1) defining the desirable weights for humans according to Metropolitan Height and Weight Tables as the midpoint of the range of the medium-frame individuals.

In another aspect, the present invention relates to a method for the treatment of diseases which are complications to overweight or obesity. These diseases or conditions include diabetes mellitus type II, hypercholesterolemia, hypertriglyceridaemia and hypertension.

In another aspect, the present invention also relates to a method of reducing adipose tissue mass/lean body mass ratio or treating overweight or obesity or complications thereof by means of subjecting the individuals to a diet regimen. The diet regimen into which the individuals may be subjected in connection with the administration of the composition may include a low carbohydrate, a low fat and a low energy regimen, e.g., a diet of from 800–2500 kcal/day.

Veterinary Use

The compositions according to the invention can also be administered to domestic animals in order to improve the performance of the animal (daily weight gain and feed utilization) or to improve carcass quality or both. Carcass quality is generally improved when the fat tissue mass/lean mass body mass ratio is decreased, i.e., when the body content of meat is increased e.g., at the expense of the body content of fat.

The improvements in performance and carcass quality are suggested to be caused by a reduced fat accretion and/or by an increased skeletal muscle accretion. In growing animals, the amount of lipid present is suggested to be governed by the relative rates of lipolysis and lipogenesis. Stimulation of lipolysis and/or inhibition of lipogencsis in fat tissue may lead to a reduced fat accretion. In vivo and in vitro studies with both pigs and ruminants may indicate that certain beta agonists stimulate lipolysis and inhibit lipogenesis in fat tissue leading to a reduced fat accretion.

Administration to an animal of the compositions according to the present invention may be useful in order to increase the lean body mass at the expense of body fat, particularly in domestic animals like pigs, hogs, cattle, sheep and poultry. The composition may be given in admixture with the feed in a suitable dose corresponding to the size of the animal.

Peptide Synthesis

The peptides can be synthesized by any suitable method, such as by exclusively solid-phase techniques, by partial solid-phase techniques, by fragment condensation or by classical solution addition. A detailed description of these methods is contained in "The Peptides, Vol. 1", Gross and Meinenhofer, Eds., Academic Press, New York, 1979. Coupling methods employed include the carbodiimide method (1,3-dicyclohexylcarbodiimide [DCC], 1-(3-dimethylaminopropyl-3-ethylcarbodiimide hydrochloride [EDCl]) with the option of racemization preventing additives (1-hydroxybenzotriazole [HOBT]), the mixed anhydride method, the azide method, the acid chloride method, the symmetrical anhydride method, the use of bis(2-oxo-3-oxazolidinyl)phosphinic chloride (BOP-Cl), and the active ester method (N-hydroxysuccinimide esters, 4-nitrophenol esters, 2,4,5-trichlorophenol esters, and the like).

For example, the techniques of exclusively solid-phase synthesis are set forth in the textbook "Solid-Phase Peptide Synthesis" Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). All of the above references are incorporated herein by reference.

Synthesis by the use of recombinant DNA techniques, for purposes of this application, should be understood to include the suitable employment of a structural gene coding for all of the tripeptide to transform a microorganism, using an expression vector including a promoter and operator together with such structural gene, and causing such transformed microorganism to express the peptide or such a synthetic peptide fragment. A non-human animal may also be used to produce the peptide by gene-farming using such a structural gene in the microinjection of embryos as described in U.S. Pat. No. 4,870,009 issued Sep. 26, 1989, incorporated herein by reference.

When the peptides are not prepared using recombinant DNA technology, they are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for NPY analogs can, for example, be prepared by attaching alpha-amino- and side-chain-protected Tyr to a BHA resin.

The compounds of the invention may be prepared by stepwise coupling of the amino acids or by coupling together fragments of dipeptide length or greater. Thus, the free carboxylic acid moiety from one amino acid or peptide fragment is activated and allowed to condense with the free nitrogen group of the second amino acid or peptide fragment. The coupling reactions are conducted in solvents such as methylene chloride ($CH_2Cl_2$), tetrahydrofuran (THF), dimethylformamide (DMF) or other such solvents.

During the coupling process, the non-participating carboxylic acids or amines on the reacting set of amino acids or peptide fragments are protected by a protecting group which can be selectively removed at a later time if desired. A detailed description of these groups and their selection and chemistry is contained in "The Peptides, Vol. 3", Gross and Meinenhofer, Eds., Academic Press, New York, 1981, incorporated herein in its entirety by reference. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl) ethoxycarbonyl, 9-fluorenylmethoxycarbonyl (Fmoc), phthaloyl, acetyl (Ac), formyl, trifluoroacetyl, and the like.

Examples of useful protective groups for the carboxylic acid include esters, such as methyl, ethyl, benzyl, t-butyl, 2,2,2-trichloroethyl, allyl, 4-nitrobenzyl, and the like. Removal of these protecting groups may be accomplished selectively by employing various acid or base catalyzed hydrolytic, hydrogenolytic, thermal or dissolving metal conditions.

Generally, peptides will be synthesized by stepwise solid phase methodology developed by using an automated Applied Biosystem Model 430A peptide synthesizer. Tertiary butyloxy-carbonyl (Boc) amino acids with benzyl or halobenzyl based side chain protecting groups (Asp & Glu with OBzl; Ser & Thr with Bzl: Cys with pMeBzl; Tyr with 2BrZ; Lys with 2ClZ; Arg with Tos; His with Bom; Trp with CHO) will be used in conjunction with phenylacetamidomethyl (PAM) resin. In the case of the synthesis of peptide amides, benzyldrylamine (BHA) or paramethylbenzylhydrylamine (MBHA) will be used instead of PAM resin.

Boc-aminoacid-PAM-resin, using Boc-aminoacyloxymethyl-phenylacetic acid and aminomethyl resin, is available commercially. The Boc-aminoacid-PAM-resin thus prepared eliminates the possibility of chain termination by tri-fluoroacetylation. Attachment to BHA or MBHA resin will be performed by way of preformed symmetrical anhydride.

Coupling and deprotection functions are generally carried out automatically by the instrument. The standard program provided by the manufacturers are modified to incorporate a double coupling procedure, first in DMF and then in $CH_2Cl_2$. Altering the polarity of the solvents improves the coupling. All amino acids, except Asn, Gln and Arg, will generally be coupled as preformed symmetrical anhydrides. Asn, Gln and Arg are double coupled as preformed 1-hydroxy-benzotriazole esters to avoid side reactions. Resin samples taken during these reactions may be assayed by quantitative procedure to determine the degree of coupling. Other standard cleaving reagents and conditions for removal of specific alpha-amino protecting groups may be used as described in Schroder & Lubke, "The Peptides" Vol. 1, pp 72–75 (Academic Press 1965), incorporated herein in its entirety by reference.

In the case of coupling unusual amino acids, suitable conditions (solubility, coupling times) will be first developed before using in automated mode. In some cases these couplings will be carried out manually (eg: pseudopeptides, N-Me-amino acids). Pseudopeptide bonds will be incorporated by the methods described earlier. The t-Boc-amino acid aldehyde will be obtained by reducing N-methoxy-N-methylamide derivatives of Boc-amino acids with $LiAlH_4$. The aldehyde obtained will be reacted immediately with the a-amino group of the peptide attached to the resin in DMF containing 1.0% HOAC in the presence of an equivalent amount of NaBH3CN. At the end of the reaction, the presence of secondary amine is tested for with ninhydrin (wine-red color). The secondary amine formed will then be blocked by reacting with 2 equivalents of Z(2-Cl)OSU, 2 equivalents of HOBT, and 4 equivalents of diisopropylethyamine until ninhydrin gives a yellow color. This way the formation of branched peptide is prevented. Coupling of sterically hindered amino acids (eg: N-Me-amino acids, CαMeLeu, Aib) will be effected by a HOAT or HATU which has been shown to be superior toBOP/HOBT.

For the final cleavage, the N-α-Boc group and the Nin-CHO will be first removed with 50% $TFA/CH_2Cl_2$ and 20% piperidine-DMF from the protected peptide resin before detaching the target peptide using HF containing p. cresol (5%). If Cys and Met are present, p. thicresol (2.5%) will also be added to the HF reaction mixture. If problems are encountered during the standard HF method, then the "low/high" HF procedure will be used.

The materials are then purified. After initial fractionation on Sephadex G-25, the peptide material will be subjected to reversed phase high performance liquid chromatography (RPLC) on $C_{18}$ Vydac columns. However, peptides may be first subjected to ion exchange chromatography before RPLC, depending upon the heterogeneity of the crude peptide. The homogeneity of the purified product may be confirmed by analytical RPLC using two different solvent systems, amino acid analysis, complete sequencing, and mass spectral analysis.

For analysis, the peptide resins are hydrolyxed using 12N HCl/HOAc/phenol (2:1:1) for 24 hours ar 110_C. The free peptides are hydrolyzed for 24 hours in 6N HCl containing 0.1% phenol or 4N methane sulfonic acid at 110_C and are quantified on a Waters Pico Tag system. Peptide hormones and fragments are then subjected to complete sequencing on an automated gas phase sequencer (Applied Biosystem, Model 470A).

For the production of a compound of the invention where any one or several of the constituent amino acids bear an N-alkyl group, specifically methyl, the corresponding N-alkyl amino acid can be prepared via the method described by Benoiton (*Can. J. Chem.,* 1977, 55:906) or Shuman ("Peptides: Proceedings of the 7th American Peptide Symposium", D. Rich, E. Gross, Eds., Pierce Chemical Co., Rockford, Ill. 1981, p 617), wherein the t-BOC- or Cbz-protected amino acid is treated with a base in the presence of a chelating agent such as a crown ether and then quenched with methyl iodide. An alternative method described by Freidinger (*J. Org. Chem.,* 1983, 48:77), in which triethylsilane reduction of the oxazolidinone of an amino acid directly produces the N-methyl derivative may also be utilized.

The reduced carbonyl amide bond surrogates can be prepared in a manner similar to that described by Martinez (*J. Med. Chem.* 1987, 30:1366). The N-alpha-t-BOC protected amino acid (with appropriate protection of side chain functional groups) is converted to the 3,5-dimethylpyrazolide, which is then reduced with lithium aluminum hydride. The resulting aldehyde is then allowed to condense with an amino acid or peptide bearing a free amino terminus. Reduction of the Schiff base which is formed as a result of the condensation is accomplished using sodium cyanoborohydride to yield the desired compound having a reduced amide bond.

Functionalization of the epsilon -amino group of the lysine (Lys) or homologous (e.g., Orn) residue is achieved via activation of the acid fragment as the active ester (N-hydroxysuccinimide, 2,4,5-trichlorophenol, etc.) or, if no other free carboxylic acid function is present on the peptide, coupling using any of the methods mentioned above is applicable. In addition, the fuictionalization of the epsilon—amino group may be accomplished by reaction with various alkyl and aryl isocyanates, as well as alkyl and aryl isothiocyanates.

The sulfuric acid esterification of the phenolic residues may be conducted using a variety of known reagents such as the pyridine-sulfuric anhydride or the pyridine-sulfur trioxide complex. Use of pyridinium acetyl sulfate as described by Penke and Rivier ("Proceedings of the 8th American Peptide Symposium", V. Hruby, D. Rich, Eds., Pierce Chemical Company, Rockford, Ill.; 1983; p. 119), may also be applied to prepare the sulfuric acid ester derivative of the tetrapeptides.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The pharmaceutically acceptable salts of the present invention can be synthesized which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

Examples of preferred salts are those with therapeutically acceptable organic acids, e.g., acetic, lactic, maleic, citirc, malic, ascorbic, succinic, benzoic, or pamoic acid, as wells as polymeric acids and salts with inorganic acids such as the hydrohalic acids, e.g., hydrocholoric and sulfric acids.

In addition, pseudopeptide bonds may, if desired, may be introduced at various positions, e.g., between amino acid residues A1–A2 or between residues A2–A3. Optically pure Boc-AA-CHO can be obtained in good yields and coupled directly to the —NH2 group of the peptide resin by published methods (Sasaki et al., *Peptides* 8:119–121, 1987; Fehrentz et al., *Synthesis* pp.676–678, 1983). The secondary amine in the pseudopeptide bond is capped with Z(2-Cl). This is introduced by reacting the peptide resin with Z(2-Cl)-OSU (2 equiv.), HOBT (2 equiv.) and DIEA (4 equiv.) for 10–60 min. The red wine color of ninhydrin with secondary amine turns yellow at the end of capping. Exemplary compounds of the present invention include:

1. Ac-Phe-Arg-Trp-NH$_2$
2. Ac-Trp-Arg-Phe-NH$_2$
3. Ac-Trp-Arg-Tyr-NH$_2$
4. Ac-Trp-Ctr-Tyr-NH$_2$
5. Ac-Trp-(Ψ)-Arg-Tyr-NH$_2$
6. Ac-Trp-Arg-Tyr-(Y)-NH$_2$
7. Ac-Arg-Tyr-NH$_2$
8. Ac-Trp-Ag-Tyr-[O(PO(OH)$_2$]-NH$_2$
9. (HO)$_2$PO-CH$_2$-CO-Trp-Arg-Tyr-NH$_2$
10. Ac-Arg-His-Tyr-NH$_2$
11. R-CO-Trp-Arg-Tyr-NH$_2$

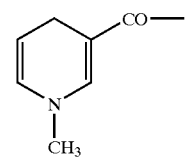

where R=

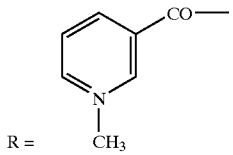

where R=

12. R-CO-Trp-Arg-Tyr-NH$_2$
13. Ac-Trp-Arg-D-Tyr-NH$_2$
14. Ac-Trp-D-Arg-Tyr-NH$_2$
15. Ac-D-Trp-Arg-Tyr-NH$_2$
16. Ac-D-Trp-D-Arg-D-Tyr-NH$_2$
17. Trp-Arg-Tyr-NH$_2$
18. Ac-Trp-Arg-Tyr-OH
19. Ac-Trp-Arg-Tyr-NH-Me
20. Ac-Trp-Arg-Tyr-NH$_2$
21. Ac-Arg-Tyr-NH$_2$
22. Bis(34/34'){[Cys$^{34}$]NPY(34–36)
23. Ac-Gln-Arg-Tyr-NH$_2$
24. H-Gln-Arg-Tyr-NH$_2$
25. Ac-Trp-h.Arg((Pr)$_2$-Tyr-NH$_2$
26. [Des-α-Amino-Trp]-Arg-Tyr-NH$_2$
27. Ac-Trp-Arg-Tic(OH)-NH$_2$
28. N-a-Indole-3-acetyl-Arg-Tyr-NH$_2$
29. AC-T ec-Arg-Tyr-NH$_2$
30. Ac-pro-Arg-Tyr-NH$_2$
31. Ac-Nal-Arg-Tyr-NH$_2$
32. Ac-Bth-Arg-Tyr-NH$_2$
33. Ac-Trp-Arg-Tyr-NH-CH$_3$
34. Ac-D-Trp-Arg-Tyr-NH$_2$
35. Ac-Trp-D-Arg-Tyr-NH$_2$
36. Ac-Trp-Arg-D-Tyr-NH$_2$
37. Ac-D-Trp-D-Arg-D-Tyr-NH$_2$ 38. Ac-[-Trp-Arg-Tyr-]$_2$-NH$_2$
39. (Ac-Cys-Trp-Arg-Tyr-NH2)$_2$ (SEQ ID NO: 2)
40. -[-CH$_2$CO-Trp-Arg-Tyr-N H2]$_2$
41. Dap-Ile-Trp-Arg-Glu-Arg-Tyr-NH$_2$ (SEQ ID NO: 3)
42. Leu-Ile-Trp-Arg-Glu-Arg-Tyr-NH$_2$ (SEQ ID NO: 4)
43. Cyclo(-Trp-Arg-Nva-Arg-Tyr-) (SEQ ID NO: 5)
43. Cyclo[-Trp-Arg-Nva-Arg-Tyr-]
44. RCO-Trp-Arg-Tyr-NH$_2$
45. Ac-Trp[CH$_2$NH]Arg-Tyr-NH$_2$
46. Ac-Trp-Arg-[CH$_2$NH]Tyr-NH$_2$
47. Ac-Arg-Tyr-NH$_2$
48. Ac-Trp-Arg-NH$_2$
49. Ac-Tcc-Arg-Tic(OH)-NH$_2$
50. Cyclo[-Trp-Arg-Tyr-Trp-Arg-Tyr-]
51. N-α-Ac-Cyclo(29/34)[D-Cys 29,34,Trp 32]NPY (29–36)-NH$_2$
52. Cyclo(30/34)[Leu30,Trp32,Glu34,]NPY(30–36)-NH$_2$
53. Cyclo(30/34)[Dap30,Trp32,Glu34,]NPY(30–36)-NH$_2$ Other analogs of the invention can be prepared as above and tested for their biological activity effectiveness as antagonists or agonists using the methods described below and those commonly known in the art.

Functional Assays

Animals, Cell Lines and Cultures, and Reagents

Any suitable in vivo or in vitro system may be utilized to assay and test the effectiveness of the compounds of the invention. Such assays may employ in vivo methods for evaluating physiological responses, e.g., blood pressure, renovascular function, feeding behavior, or circadian rhythm, or in vivo biochemical systems evaluating receptor binding in a suitable cell line, e.g. SK-N-MC (ATCC HBT 10) or SK-N-BE(2) (Barnes et al. In Vitro, 17: 619 631, 1981); or in isolated cells, e.g., cells isolated from the spleen, kidney, heart or brain. A number of in vivo and in vitro biochemical systems known to those skilled in the art are available for testing antagonists to hypothalamic NPY receptors, e.g. the Y-1, Y-2, and Y-3 receptor categories. Described below are assay methods which can be utilized with cell lines such as SK-N-MC and SK-N-BE2 or isolated cardiac membranes which possess the high-affinity hypothalamic NPY receptor sites. Other systems are also known for evaluating NPY antagonists to the hypothalamic NPY receptor, e.g. VSM cells (Sheikh et el, Am. J. Physiol. 260: G250 G257, 1991) and HEL cells (Motulsky et al. Amer. J. Physiol. 255: E880–E885, 1988); Y-2 receptor, e.g., kidney (Sheikh et al., Am. J. Physiol 26:F978–F984), spleen (Lunberg et al., Eur. J. Pharmal. 145:21–29, 1988), dorsal root ganglion (Bleakman et al., Br. J. Pharmal. 103:1781–1789, 1991) and hippocampal cells (Sheikh et al., J. Biol. Chem. 265:8304 8310, 1990); and Y-3 receptors, e.g., in cardiac ventricular membranes (Balasubramaniam et al., Peptides 11: 545–550, 1990), chromaffin cells, rat gastric mucosa (Michel, M. C., *Trends in Pharmol. Sci.* 12: 389–394, 1991) and brain stem.

In Vitro Biochemical Assays

The ability of the compounds of the invention to act as antagonists of NPY can be demonstrated by any number of methods known in the art. For example, the compounds can be shown to compete with iodinated neuropeptide Y for receptors using the methods described by Lundberg et al. (*Eur. J. Pharmol.* 145: 21–29, 1988); Gordon et al. (*J. Neurochemistry* 55:506–513, 1990); Walker et al. (*Mol. Pharmacol.* 34:779 792, 1988), Balasubramaniam et al. (*Peptides* 10:1283–1286, 1989).

In one example demonstrating antagonists to hypothalamic NPY receptors, rat hypothalmus was isolated and the membranes were prepared for binding and adenylate cyclase studies according to standard methods (Unden et al. 1984. *Eur. J. Biochem* 145: 525–530; Westlind-Danielsson et al., *Neurosci. Lett.* 74: 237–242 (1987)). Displacement studies are performed in a total volume of 0.25 ml 20 mM HEPES buffer, pH 7.4, containing 1% bovine serum albumin, 0.1% bacitracin, 300 μm PMSF and 5 KIU/ml aprotinin. In a standard assay, 100 μg of membrane/tube is incubated in a shaking water bath at 24_C for 45 min with [$^{125}$I-Tyr]-NPY (20,000 CPM) as described by Balasubramaniam et al., (*Peptides* 11: 545–550, 1990), in the presence of increasing concentrations of NPY (10 μOsM). At the end of incubation, 1.0 ml of iced cold buffer is added, centrifuged at 10,000×g for 10 min, and the supernatant removed by aspiration. The tube containing the pellet is counted for bound radioactivity in a micromedic gamma counter.

An example of assaying adenylate cyclase activity of hypothalamic and cerebral cortex membranes is now described.

Adenylate cyclase activity of the hypothalamic and cerebral cortex mebranes is determined by incubating 50 μg of membranes in a total volume of 0.20 ml Tris-HCμ 30 mM pH 7.4 buffer containing 150 mM NaCl, 8.25 mM MgCl2, 0.75 mM EGTA, 1.5 theophylline, 20 μg/ml aprotinin, 100 μg/ml bacitracin, 1 mg/ml bovine serum albumin, 1 mM ATP, 20 mM creatine phosphate, 1 mg/ml phosphocreatine kinase, 10 μM isopretemol, 10 μM GTP, and various concentrations of peptides (0–10 μM). After incubating the mixture at 35_C for 15 min in a shaking water bath, the reaction is arrested by the addition of 100 μM EDTA and boiling for 3 min. cAMP is extracted and quantitated by radioimmunoassay. All the points in the binding and adenlyate cyclase are the means of at least three parallel experiments performed in duplicate.

In Vivo Assays

Any suitable in vivo model system can be used to evaluate the antagonistic properties of the compounds of the invention. Such models, without limitation, include those used to evaluate feeding and memory behavior (Flood et al., *Peptides* 10:963–966), and vasoconstriction and hypertension (Balasubramaniam et al. *Biochem et Biophys Acta* 997: 176–188, (1989)).

Thus, in one example, feeding studies are performed using Spraque Dawley rats (350–450 g) with paraventricular hypothalmic cannulae to investigate effecta of NPY analogs (Chance et al., *Peptides* 10: 1283, 1286 (1989)).

The following Examples set forth preferred methods for synthesizing tripeptides by the solid-phase technique and generally is in accordance with the procedure set forth in U.S. Pat. No. 4,415,558 to Vale, et al., issued Nov. 15, 1983, the disclosure of which is incorporated herein by reference.

EXAMPLES

Example I

The synthesis of N-alpha-Ac-Trp-Arg-Tyr-NH$_2$, is conducted in a stepwise manner on a methylbenzhydrylamine hydrochloride resin, such as available from Bachem, Inc., having a substitution range of about 0.1 to 0.5 mmoles/g resin. The synthesis is performed on an automatic Applied Biosystems, Model 430A, peptide synthesizer using the program supplied by the manufacturer. Briefly, MBHA resin is placed in the reaction vessel of the peptide synthesizer, and the amino acids, Boc-Tyr(2BrZ)-OH, Boc-Arg(Tos)-OH and Boc-Trp(CHO)-OH, are sequentially coupled using preformed HOBT ester (2.0 mmol) according to the program provided by the ABI 430A synthesizer. At the end of the synthesis, alpha-amino group is acetylated with acetic anhydride and the in-CHO group removed by stirring with 20% piperidine in DMF for 2 hours. The peptide is detached from the resin by treating with HF containing 5% p. cresol for about 1 h at about –2_C. HF is evacuated under vacuo and the residue transferred to a fritted funnel with diethyl ether and is washed repeatedly with diethyl ether. The crude peptide extracted with acetic acid (10 ml×2) is diluted to 10% and lyophilized. The peptide is then purified to homogeneity by reversed phase chromatography on a C-18 semi-preparative column (250×10 mm) using the buffer systems 0.1% TFA-$H_2O$ and 60% $CH_3CN$ in 0.1% TFA-$H_2O$. The peptides are characterized by amino acid and mass spectral analysis.

Example II

The peptide N-alpha-Ac-Trp-[$CH_2NH$]-Arg-Tyr-$NH_2$ is synthesized using the method as described in Example I. However, Boc-Trp-CHO, (Synthesis 676–679, 1983), is coupled to H-Arg(Tos)-Tyr(2br-Z)-MBHA-Resin by reductive alkylation in the presence of 1.0% HOAc and 1.0 equiv. of $NaBH_3CN$ in DMF. The crude peptide obtained by HF cleavage is purified as described earlier. Boc-Arg(Z)2-OH is used to prepare the corresponding aldehyde and synthesize N-alpha-Ac-Trp-Arg-[$CH_2NH$]-TYr-$NH_2$.

Example III

A peptide dimer is synthesized using the general method as described in Example I, except that after the synthesis of Trp(CHO)-Arg(Tos)-Tyr(2-Br-Z)-MBHA-Resin, the peptide resin is reacted with half an equivalent N, N-Bis-Boc-Cystine, succinic acid, maleic acid or N2, N6di-Boc-Pim (Pim=2,6-diaminopimelic acid), in the presence of 1 equivalent of DCC, HOBT and DEA until the ninhydrin test is negative. The uncoupled alpha-amino group may be acetylated with acetic anhydride. The peptides are then cleaved and purified as described above.

Example IV

To study the feeding patterns of animals treated with the tripeptides, rats with intrahypothala nic cannulae are used. Sprague-Dawley rats weighing about 250–350 g are anesthetized with pentobarbital (45 mg.kg) and 24 ga stainless steel cannulae are surgically implanted into the perifomical hypothalamus athe the following stereotaxic coordinates taken from the interaural line: A=6.5, L=0.8, V=–2.0 mm. Investigations are performed two weeks after surgery.

A total of 32 rats arc divided into four groups in the inital screening. These include control (artificial cerebral spinal fluid, CSF), T-83 (Ac-Tcc-Arg-Tyr-$NH_2$), T-84 (N-a-indole-3-acetyl-Arg-Tyr-$NH_2$), and T-91 (Ac-Trp-Arg-Tic(OH)-$NH_2$). Articifial CSF (CSF, 0.5 μl) or peptides (0.5–20.0 μg) in CSF are injected via the cannulae directly into the hypothalamus and the food intake of rat chow is monitored for 1,2 and 4 hour periods. Water is available throughout the experiment. The results arc shown in FIG. 1.

Example V

Figure 2:
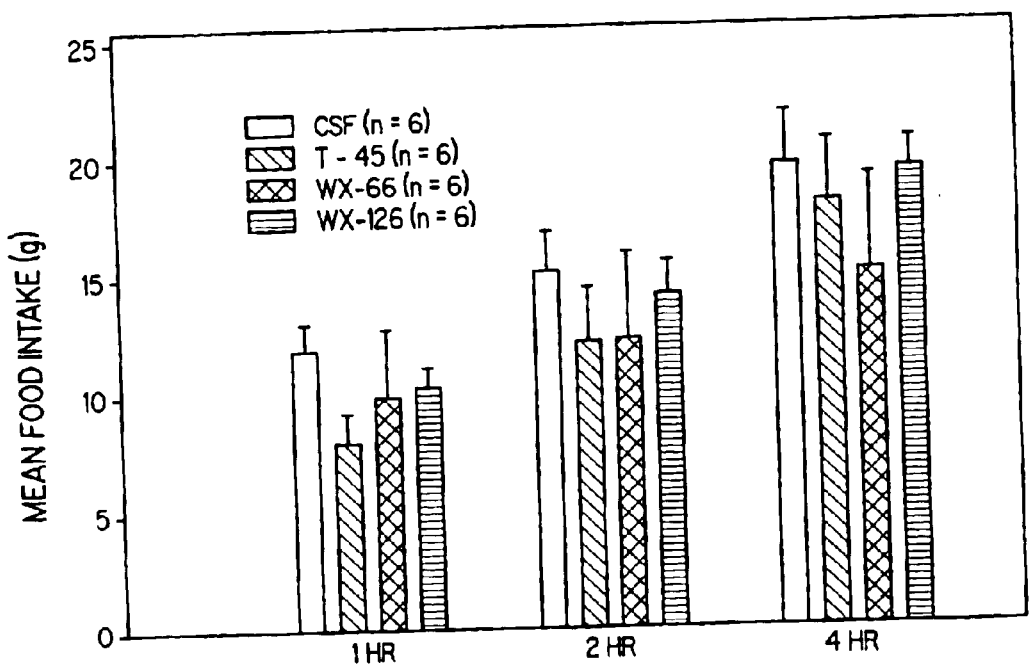
FIG. 2. A graph representing the feeding patterns of animals treated with the tripeptides by intrahypothalamic cannulae. The compounds tested include control (artificial cerebral spinal fluid, CSF), T-45 (Bis(34/34'){[Cys34]NPY (34–36)}), WX-66 (Ac-D-Trp-Arg-Tyr-NH$_2$), and WX-126 (Ac-Gln-Arg-Tyr-NH$_2$).

A feeding experiment is performed as in Example IV except that the 32 rats are divided into four groups which include control (artificial cerebral spinal fluid, CSF), T-45 (Bis(34/34'){[Cys34]NPY(34–36)}), WX-66 (Ac-D-Trp-Arg-Tyr-$NH_2$), and WX-126 (Ac-Gln-Arg-Tyr-$NH_2$). The results are shown in FIG. 2.

Example VI

Figure 3:
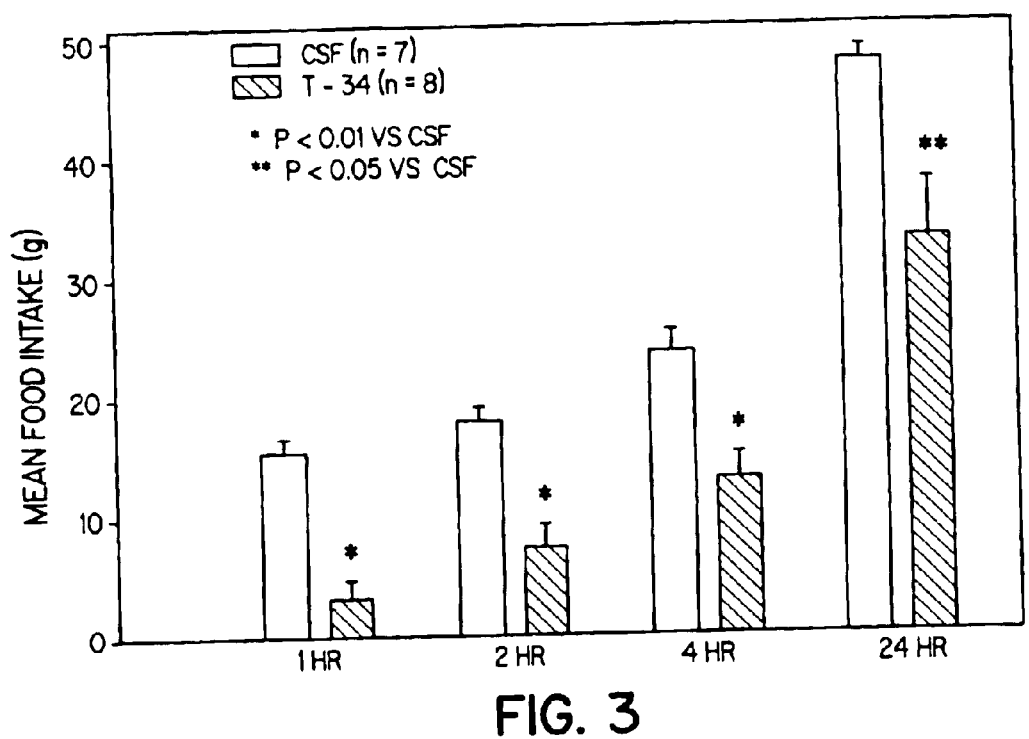
FIG. 3. A graph representing the feeding patterns of animals treated with the tripeptides by intrahypothalamic cannulae. The compounds tested include control (artificial cerebral spinal fluid, CSF) and T-34 (N-Ac-Trp-Arg-Tyr-NH$_2$).

A feeding experiment is performed as in Example IV except that 15 rats are divided into two groups which include control (artificial cerebral spinal fluid, CSF) and T-34 (N-Ac-Trp-Arg-Tyr-$NH_2$). Food intake of rat chow is monitored for 1,2,4 and 24 hour periods. The results are shown in FIG. 3.

What is claimed is:

1. A therapeutic composition comprising:
a therapeutically effective amount of a compound having the formula:

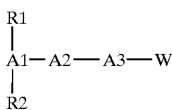

wherein:
each R1 and R2, independently, is H, C1–C12 alkyl, C6–C18 aryl, C1–C18 acyl, C7–C18 aralkyl, C7–C18 alkaryl or a dihydrotrigonellinate group;

A1 is a D or L-amino acid selected from the group consisting of Cys, Leu, Dap, Trp, Gln, a tethered amino acid with an indole ring, Phe, Hyp, a derivative of Trp selected from the group consisting of N-Me-Trp, nor Trp, beta Me-Trp, 2-Cl-Trp, and 5-X-Trp, where X is selected from the group consisting of CN, Br, $NH_2$, COOH, $CH_2NH_2$ and $CH_2$-$CH_2NH_2$; CαMe-Trp, CαMe-Gln, Des-amino-Trp, Pyr, Bth, Nal, Tcc, Asn, Nva, Abu, Tyr, Tic-OH, Tip, and Dip;

A2 is a D or L-amino acid selected from the group consisting of Cys, Trp, Arg, Nα-Me-Arg, CαMe-Arg, Orn, Cit, hArg(R)2, where R is selected from the group consisting of hydrogen, alkyl, aryl, aralkyl, and alkylaryl, Lys-ε-NH-R, where R is selected from the group consisting of alkyl, aryl, aralkyl, and alkylaryl;

A3 is a D or L-amino acid selected from the group consisting of Glu, N-Me-Tyr, CαMe-Tyr, Tic-OH, Tic, Dip, Trp, Phe, des-carboxylic-Tyr (tyramine), and Tyr-(R), where R is hydrogen or lipophilic group;

W is OH, —N—R3R4, or OR5, where R3, R4 and R5, independently, is H, C1–C12 alkyl, C6–C18 aryl, C1–C12 acyl, C7–C18 aralkyl, or C7–C18 alkaryl, or a pharmaceutically acceptable salt thereof; and each bond between two amino acids or amino acid derivatives, represented by a dash ("–"), can be either a peptide bond or a pseudopeptide bond; and a pharmaceutically acceptable carrier substance;

wherein said therapeutically effective amount of said compound in said composition attenuates Neuropeptide Y (NPY) mediated physical responses.

2. The compound of claim 1, wherein said compound has a formula consisting of N-α-Ac-Trp-Arg-Tyr-$NH_2$.

3. The compound of claim 1, wherein said compound is conjugated to a carrier selected from the group consisting of cationized albumin and polylysine.

4. The compound of claim 1, wherein the said bond between two amino acids or amino acid derivatives is selected from the group consisting of C(O)NH, $CH_2NH$, $CH_2$—S, $CH_2$—O, $CH_2$—CO, and $CH_2CH_2$.

5. The compound of claim 4, wherein a pseudopeptide bond is positioned between A1 and A2.

6. The compound of claim 5, wherein a pseudopeptide bond is positioned between A2 and A3.

7. The composition of claim 1, wherein said composition is in the form of a pill, tablet, or capsule for oral administration.

8. The composition of claim 1, wherein said composition is in the form of a liquid for oral administration.

9. The composition of claim 1, wherein said composition is in the form of a liquid for nasal administration as drops or spray.

10. The composition of claim 1, wherein said composition is in the form of a liquid for intravenous, subcutaneous, parenteral, or intraperitoneal administration.

11. The composition of claim 1, wherein said composition is in the form of a biodegradable sustained-release composition for intramuscular administration.

12. The composition of claim 1, wherein said composition includes a lipophilic salt and is suitable for administration in the form of an oil emulsion or dispersion.

* * * * *

UNITED STATES PATENT AND TRADEMARK OFFICE
CERTIFICATE OF CORRECTION

PATENT NO.    : 6,737,408 B1
DATED         : May 18, 2004
INVENTOR(S)   : Balasubramaniam et al.

It is certified that error appears in the above-identified patent and that said Letters Patent is hereby corrected as shown below:

Title page,
Item [56], References Cited, OTHER PUBLICATIONS,
"A." reference, "Balasubramanium" should be -- Balasubramaniam --.
"M. Heilig" reference, "Dept. of Psychiatry and Neurochemistry, University of Lund, Lund, Sweden, Mar. 17,1990, pp. 95-114" should be -- Acta Psychiatr. Scand, vol. 82, 1990, 95-114 --.
"Shin-ichi" reference, "Y.induced" should be -- Y-induced --.
"William M. Pardridge" reference, "vol. 126, 1990" should be -- vol. 126, No. 2, 1990 --.
"Thue" reference, "Annuals" should be -- Ann.--.

Column 1,
Line 41, "dope minergic" should be -- dopaminergic --.
Line 48, "with the actions other drugs" should be -- with the actions of other drugs --.
Line 65, "Amsterd in -New York-Oxford" should be -- Amsterdam-New York-Oxford --.

Column 2,
Line 32, "A. Foumier" should be -- A. Fournier --.
Line 40, "Humana Press, Inc ," should be -- Humana Press, Inc., --.
Line 48, "Y.-S. Zhang" should be -- Y. S. Zhang --.

Column 3,
Line 9, "H. . Thogersen" should be -- H. Thogersen, --.

Column 4,
Line 12, "J. D. Rosarnond" should be -- J. D. Rosamond --.
Line 61, "CaMe-Trp, CaMe-Gin" should be -- C$\alpha$Me-Trp, C$\alpha$Me-Gln --.

Column 5,
Line 7, "des- arboxylic-Tyr" should be -- des-carboxylic-Tyr --.
Line 10, "(where R3" should be -- where R3 --.
Line 11, "independently, is" should be -- independently are --.
Line 12, "(e-g-, phenyl)" should be -- (e.g., phenyl) --.

Column 6,
Line 18, "(N-a-indole-3-acetyl-" should be -- (N-$\alpha$-indole-3-acetyl- --

UNITED STATES PATENT AND TRADEMARK OFFICE
CERTIFICATE OF CORRECTION

PATENT NO. : 6,737,408 B1
DATED : May 18, 2004
INVENTOR(S) : Balasubramaniam et al.

It is certified that error appears in the above-identified patent and that said Letters Patent is hereby corrected as shown below:

Column 7,
Line 4, "(where R3" should be -- where R3 --.
Line 5, "independently, is" should be -- independently, are --.
Line 49, "formula I-III)" should be -- formula (I-III) --.
Line 53, "the invention features" should be -- the invention featuring --.

Column 8,
Line 20, "in the form a pill" should be -- in the form of a pill --.
Line 25, "administration biodegradable" should be -- administration is biodegradable --.
Line 44, "R is -CH3" and should read -- R is $CH_3$ --.

Column 9,
Line 3, "Phenytalanine" should be -- Phenylalanine --.
Line 11, "(8-aminoctanoic acid:" should be -- (8-aminooctanoic acid) --.
Line 28, "arboxylic acid" should be -- carboxylic acid --.
Line 34, "Citrutine" should be -- Citruline --.
Line 36, "diaminopimelicacid" should be -- diaminopimelic acid --.
Line 63, "The terms "CI-C-18-alkyl" as used herein refer to" should be -- The term "C1-C-18-alkyl" as used herein refers to --.

Column 10,
Line 9, "C1-C4alkyl" should be -- C1-C4-alkyl --.
Line 22, "-OSO3H" should be -- $OSO_3H$ --.

Column 11,
Line 16, "1000 mg a day and more usually" should be -- 1000 mg a day and more, usually --.
Line 24, "administer.a" should be -- administer a --.
Line 25, "particular compounds," should be -- particular compound, --.
Line 40, "ex ample" should be -- example --.
Line 53, "tablets , or" should be -- tablets, or --.
Line 62 reads "suspension provide the" and should read -- suspension provides the --.

Column 12,
Line 2, "a hexitol or a hexitol anhydrides," should be -- a hexitol or hexitol anhydrides --.
Line 54, "typically" should be -- typical --.
Line 54, "enhances" should be -- enhancers --.

UNITED STATES PATENT AND TRADEMARK OFFICE
CERTIFICATE OF CORRECTION

PATENT NO. : 6,737,408 B1
DATED : May 18, 2004
INVENTOR(S) : Balasubramaniam et al.

It is certified that error appears in the above-identified patent and that said Letters Patent is hereby corrected as shown below:

Column 14,
Line 12, "lipogencis" should be -- lipogenesis --.

Column 15,
Line 45, "Bzl:" should be -- Bzl; --.
Lines 59-60, "program" should be -- programs --.

Column 16,
Line 12, "eralier" should be -- earlier --.
Line 16, "a-amino" should be -- α-amino --.
Line 18, "NaBH3CN" should be -- $NaBH_3CN$ --.
Line 27, "toBOP/HOBT" should be -- to BOP/HOBT --.
Line 46, "hydrolyxed" should be - hydrolyzed --.
Lines 47 and 49, "110_C" should be -- 110°C --.

Column 17,
Line 19, "fuictionalization" should be -- functionalization --.
Line 62, "citirc" should be -- citric --.
Line 63, "as wells as" should be -- as well as --.
Line 66, "may, if desired, may be" should be -- may, if desired, be --.

Column 18,
Line 17, "Ac-Trp-Arg-Tyr-(Y)-NH" should be -- Ac-Trp-Arg-Tyr-(Ψ)-NH --.
Line 29, "R=" should be -- where R= --.
Line 31, add -- = 12. R-CO-Trp-Arg-Tyr-$NH_2$ --.
Line 38, delete "R=".
Line 41, delete "where R=."
Line 42, delete "12. R-CO-Trp-Arg-Tyr-$NH_2$."
Line 52, "{[$Cys^{34}$ ]" should be -- [Cys34] --.
Line 55, "Arg(($Pr)_2$" should be -- Arg$(Pr)_2$ --.
Line 58, "N-a-Indole-3" should be -- N-α-Indole-3 --.
Line 59, "Ac-T ec-Arg-Tyr" should be -- Ac-Tcc-Arg-Tyr --.
Line 60, "Ac-pro-Arg" should be -- Ac-Pro-Arg --.

UNITED STATES PATENT AND TRADEMARK OFFICE
CERTIFICATE OF CORRECTION

PATENT NO. : 6,737,408 B1
DATED : May 18, 2004
INVENTOR(S) : Balasubramaniam et al.

It is certified that error appears in the above-identified patent and that said Letters Patent is hereby corrected as shown below:

Column 19,
Line 1, "38. Ac-[-Trp-Arg-Tyr-]$_2$ -NH" should be -- 38. Ac-[-Trp-Arg-Tyr-]$_2$ -NH (SEQ ID NO: 6) --.
Line 7, "Cyclo[-Trp-Arg-Nva-Arg Tyr-]".
Line 14, "Cyclo[-Trp-Arg-Tyr-Trp-Arg-Tyr-)" should be
-- Cyclo[-Trp-Arg-Tyr-Trp-Arg-Tyr-] (SEQ ID NO: 7) --.

Column 20,
Line 9, "24_C" should be -- 24°C --.
Line 20, "Adenlyate" should be -- Adenylate --.
Line 21, "mebranes" should be -- membranes --.
Line 23, "MgCl2" should be -- MgCl$_2$ --.
Line 27, "isopretemol" should be -- isopreternol --.
Line 29, "35_C" should be -- 35°C --.
Line 32, "adenlyate" should be -- adenylate --.
Line 44, "Spraque" should be -- Sprague --.

Column 21,
Line 5, "-2_C" should be -- -2°C --.
Line 25, "Tyr-NH" should be -- -Tyr-NH --.
Line 33, "N6di-Boc-Pim" should be -- N6-di-Boc-Pim --.
Line 35, "DEA" should be -- DIEA --.
Line 60, "MOD RES" should be -- MOD_RES --.

Column 22,
Line 4, "intrahypoythala nic" should be -- intrahypothalamic --.
Line 6, "(45 mg.kg)" should be -- 45 mg/kg --.
Line 7, "perifomical" should be -- perifomical --.
Line 8, "athe the" should be -- at the --.
Line 12, "arc divided" should be -- are divided --.
Line 14, "(N-a-indole-3-" should be -- (N-α-indole-3 --.
Line 20, "arc shown" should be -- are shown --.

Column 23,
Line 8, "<221> NAME/KEY: MOD RES" should be -- <221> NAME/KEY: MOD_RES --.

UNITED STATES PATENT AND TRADEMARK OFFICE
CERTIFICATE OF CORRECTION

PATENT NO. : 6,737,408 B1
DATED : May 18, 2004
INVENTOR(S) : Balasubramaniam et al.

It is certified that error appears in the above-identified patent and that said Letters Patent is hereby corrected as shown below:

Column 26,
Line 4, "physical" should be -- physiological --.

Signed and Sealed this

Third Day of May, 2005

JON W. DUDAS
*Director of the United States Patent and Trademark Office*